United States Patent [19]

Butman et al.

[11] Patent Number: 4,950,589
[45] Date of Patent: Aug. 21, 1990

[54] GENUS-SPECIFIC LISTERIA ANTIGEN IDENTIFIED BY MONOCLONAL ANTIBODIES

[75] Inventors: Bryan T. Butman, Walkersville; Jerome A. Mattingly, Gaithersburg, both of Md.

[73] Assignee: Akzo n.v., Arnhem, Netherlands

[21] Appl. No.: 83,619

[22] Filed: Aug. 10, 1987

[51] Int. Cl.$^5$ ................. G01N 33/569; G01N 33/577
[52] U.S. Cl. ........................................ 435/7; 435/810; 436/548; 530/350; 530/387; 530/806; 530/809; 530/825
[58] Field of Search ................... 435/7, 810; 436/548; 530/350, 387, 806, 809, 825

[56] References Cited

PUBLICATIONS

Farber et al., *Journ. Food Protect.*, 50, 479–484, 1987.
Khan et al., *Zbl. Bakt. Hyg., I. Abt. Orig. A.*, 239, 62–69, 1977.
Seeliger et al., In Sneath et al. (Eds), Bergy's Manual of systematic Bacteriology, vol. 2, 6th Ed., Williams & Wilkins, 1984, pp. 1235–1237.
Sevier et al., *Clinical Chem.*, 27, 1797–1806, 1981.

Primary Examiner—Sam Rosen
Assistant Examiner—David A. Saunders
Attorney, Agent, or Firm—William M. Blackstone

[57] ABSTRACT

Antigens characteristic of all species of Listeria except *L. denitrificans* comprising proteins found in Listeria heat extracts, the major antigen having a molecular weight of from about 30 to about 38KD and comprising three immunogenically different epitopes and others comprising proteins having a molecular weight range of approximately 17KD to the major antigen and comprising an epitope immunoreactive with antibodies that are also reactive with one of the three epitopes on the 30 to about 38KD protein. The invention also comprises mouse monoclonal antibodies specifically reactive with the identified epitopes on these antigens.

16 Claims, 4 Drawing Sheets

TOT. PROT.
(L. MON.)
L. MURRAYI
L. SEELIGERI
L. IVANOVII
L. GRAYI
L. INNOCUA
L. MONOCYT.(4b)
L. MON. (4e)
L. MON. (4d)
L. MON. (4c)
L. MON. (4a)
L. MON. (2)
L. MON. (1)
L. DENITRIF.

GENUS-SPECIFIC LISTERIA ANTIGEN IDENTIFIED BY MONOCLONAL ANTIBODIES

BACKGROUND OF THE INVENTION

*Listeria monocytogenes* has received increasing attention as a human pathogen. Several documented outbreaks of listeriosis have been reported that have identified Listeria-contaminated food as the source of infection. In 1981 there was a major outbreak associated with cabbage, in 1983 with milk, and in 1985 there were more than 100 cases attributed to contaminated cheese.

The FDA has indicated that there is zero tolerance for Listeria in food. There have been several recent FDA recalls of products containing Listeria, generally consisting of dairy products, notably cheese and ice cream, some of which were imported. There have also been numerous company-initiated food product recalls.

Although there clearly exists a need for a reliable method to identify Listeria-contaminated food products, there is currently no easy or universally accepted method of culturing or confirming Listeria. The Association of Official Analytical Chemists (AOAC), the organization which validates methods of analysis for the food industry, has yet to approve any method to culture Listeria from food products. The FDA-suggested method requires lengthy cold enrichment culturing prior to testing. Other methods require elaborate instrumentation for data analysis.

Listeria is a gram-positive, non-sporeforming, motile rod, which has the capacity to grow over a wide range of temperatures (4° C. to 45° C.). It has been reported to be antigenically related to other gram positive organisms such as *Staphylococcus aureus* and *Streptococcus fecalis*. Consequently, an immunodiagnostic approach to Listeria identification requires very specific antibodies. We have produced and characterized a series of murine monoclonal antibodies that identify a genus-specific Listeria antigen, with which we have been successful in developing a diagnostic assay.

SUMMARY OF THE INVENTION

We have produced mouse monoclonal antibodies that react with Listeria heat extracts from all species of Listeria except *L. denitrificans*. These monoclonals are all reactive with one particular protein having a molecular weight range of from about 30 to about 38 KD, measured under both reducing and non-reducing conditions. This antigen was identified in all species, with some slight molecular size variation between species. This antigen is characterized by having three immunogenic epitopes. Thus the antibodies generated were specifically reactive with either one of the three epitopes. Lower molecular weight antigens were identified having a molecular weight range of about 17 KD to about 30 KD, which are characterized by containing an epitope having the same immunoreactivity as one of the three epitopes in the 30 to 38 KD protein.

DESCRIPTION OF THE PREFERRED EMBODIMENTS

The current FDA approved detection method for Listeria in many food products requires cold-enrichment culturing for at least seven days prior to testing. This is laborious and time consuming and delays the release of the finished product. At the present time there is no quick and accurate test for Listeria available, such as one using monoclonal antibodies.

Toward the goal of developing a rapid immunoassay for Listeria detection, we have developed and characterized monoclonal antibodies that show specificity for Listeria. We have extensively tested these monoclonal antibodies by enzyme linked immunosorbent assays (ELISA) for broad range reactivity with a panel of Listeria serotypes (1-5). We have identified fifteen monoclonal antibodies that react with heat extracts from all species of Listeria, including *L. monocytogenes* (Serotypes 1-4), *L. grayi* (Serotype 5), *L. ivanovii*, *L. murrayi*, *L. seeligeri*, and *L. innocua*, with the sole exception of *L. denitrificans*. *L. denitrificans*, which was obtained from the ATCC, has been reported to be "inconsistent with the description of the genus Listeria" (ATCC Manual, 1985). Therefore, the non-reactivity of the anti-Listeria monoclonal antibodies with this heat extract may be because *L. denitrificans* is incorrectly classified in the genus Listeria.

We confirmed the specificity for Listeria by ELISA testing the monoclonal antibodies against a comprehensive panel of relevant gram positive and gram negative organisms, many of which often grow out of pre-enrichment media when culturing for Listeria (Table 2). As all 15 monoclonals failed to react significantly with any of the non-Listeria heat extracts, it can be concluded that they recognize a genus-specific antigen of Listeria.

Of the monoclonal antibodies specific to Listeria, we found the $IgG_{2a}$ monoclonals to also show reactivity with *S. aureus* (Table 3); however, this was shown to be due to the presence of cell wall material in the heat extract, which bound the antibodies. As this was eliminated by centrifugation, we concluded that the binding of the $IgG_{2a}$ monoclonals to *S. aureus* was mediated by protein-A in the cell wall, which is known to bind $IgG_2$ antibodies through their $F_c$ portion (Goding, 1978). Our conclusion was supported by the fact that none of the Listeria-specific $IgG_1$ monoclonal antibodies, which generally bind Protein A with less affinity than $IgG_{2a}$ (Goding, 1978), produced a positive reaction with *S. aureus*. We also identified a monoclonal antibody, 10-7C, that appeared to recognize all gram positive organisms. 10-7C continued to react with both Listeria and *S. aureus* heat extracts despite centrifugation.

We characterized antigens with which our Listeria specific monoclonals reacted by Western blot analysis. All 15 Listeria-specific monoclonal antibodies recognized a protein in the molecular weight range of 30 to 38 KD under both reducing and non-reducing conditions. The $IgG_{2a}$ monoclonals and some of the $IgG_1$ monoclonals also bound to lower molecular weight antigens ranging in size from approximately 17 KD to the size of the major antigen. The major antigen was found in two molecular weight ranges, depending upon the Listeria species tested. In *L. monocytogenes* (Serotypes 1-4), *L. ivanovii*, *L. seeligeri*, and *L. innocua*, this antigen is approximately 30 to 34 KD. In *L. grayi* and *L. murrayi* it is approximately 34 to 38 KD.

There appears to be at least three groups of Listeria-specific monoclonal antibodies based upon subisotype analysis and ELISA and Western blot results. One group (Group I) consists of $IgG_1$ monoclonals, which generally produced lower ELISA signals and appears to react only with the genus specific antigen in the range of 30 to 38 KD (see FIG. 1, for example, monoclonal antibody 9-5E). The second group (Group II) consists of $IgG_1$ monoclonals which generally produced intermediate ELISA signals and bound primarily to the 30 to 38 KD antigen, but also recognized 2 to 4 lower molecular weight antigens (see FIG. 1, for example, monoclonal antibody 10-12C). The third group (Group III consists of $IgG_{2a}$ monoclonals, which generally produced higher ELISA readings and bound primarily to the 30 to 38 KD antigen, but also recognized at least 4 lower molecular weight antigens (see FIG. 1, for example, monoclonal antibody 10-2A). The existence of at least three epitope specificities was further substantiated by the successful utilization of several of these monoclonals in a 2-site sandwich ELISA, which showed the identical specificity as described here for the individual monoclonals. In addition, the gram positive-specific monoclonal, 10-7C, was characterized as clearly binding to a different antigen than the Listeria-specific monoclonal antibodies, based upon both ELISA and Western blot results.

We generated and identified 15 Listeria-specific monoclonal antibodies that define a genus-specific protein antigen in the range of 30 to 34 KD or 34 to 38 KD, depending on the species. Their use in a rapid sandwich immunoassay enables the convenient detection of Listeria in contaminated food products. In the examples that follow the immunoassay was prepared in an ELISA format. However, any label and method of detection or measurement may be selected by the skilled practitioner, such as RIA, particle agglutination, fluorescent immunoassay or precipitation reactions.

EXAMPLES

Bacterial Cultures

Cultures (see Table 1) of Listeria and other organisms were maintained on agar slants or as stab cultures at 4° C. on medium containing Tryptic Soy Broth (TSB) (BBL)+0.6% yeast extract (YE) (BBL)+1.5% Bacto-agar (Difco).

TABLE 1

| Bacterial Cultures | | | |
|---|---|---|---|
| Designation | Organism | Type | Strain |
| L1 | Listeria monocytogenes | — | — |
| L5 | L. innocua | — | — |
| L8 | L. monocytogenes | 1a | V-7 |
| SB1 | L. ivanovii | 5 | KC1714 |
| SB2 | L. ivanovii | — | ATCC 19919 |
| SB3 | L. monocytogenes | 3b | SE35 |
| SB4 | L. monocytogenes | 3a | KC 1708 |
| SB5 | L. monocytogenes | 1a | V-7 |
| SB6 | L. monocytogenes | — | F3406 |
| SB7 | L. monocytogenes | 4b | F9061 |
| SB8 | L. monocytogenes | 1/2a | F9014 |
| SB9 | L. monocytogenes | 3b | SE31 |
| SB10 | L. monocytogenes | 1b | Brie 1 |
| SB11 | L. monocytogenes | 4b | KC1710 |
| SB12 | L. monocytogenes | 1/2a | F9109 |
| SB13 | L. monocytogenes | — | F2379 |
| SB14 | L. monocytogenes | 4b | F9089 |
| SB15 | L. monocytogenes | 1/2b | F8964 |
| SB16 | L. monocytogenes | 1a | Brie 18 |
| SB17 | L. monocytogenes | 3 | ATCC 19113 |
| SB18 | L. monocytogenes | 3a | F8828 |
| SB19 | L. monocytogenes | 4b | Scott A |
| SB20 | L. monocytogenes | 3b | F9035 |
| SB21 | L. monocytogenes | 1/2b | F9069 |
| SB22 | L. innocua | — | ATCC 33091 |
| A1 | L. denitrificans | — | ATCC 14870 |
| A2 | L. grayi | — | ATCC 25400 |
| A3 | L. monocytogenes | 1 | ATCC 19111 |
| A4 | L. monocytogenes | 2 | ATCC 19112 |
| A5 | L. monocytogenes | 4a | ATCC 19114 |
| A6 | L. monocytogenes | 4c | ATCC 19116 |
| A7 | L. monocytogenes | 4d | ATCC 19117 |
| A8 | L. monocytogenes | 4e | ATCC 19118 |
| A9 | L. denitrificans | — | ATCC 14870 |
| A10 | L. grayi | 5 | ATCC 25400 |
| A11 | L. murrayi | — | ATCC 25401 |
| A12 | L. seeligeri | — | ATCC 35967 |
| L6 | Streptococcus sp | — | — |
| A13 | S. cremoris | — | ATCC 19257 |
| A14 | S. bovis | — | ATCC 27960 |
| A15 | S. pyogenes | — | ATCC 19615 |
| A16 | S. thermophilus | — | ATCC 14485 |
| A17 | S. fecalis | — | ATCC 828 |
| L7 | Pseudomonas fluorescens | — | — |
| A18 | P. fluorescens | — | ATCC 949 |
| A19 | Micrococcus varians | — | ATCC 15306 |
| A20 | Staphylococcus aureus | — | ATCC 12598 |
| A21 | S. epidermidis | — | ATCC 155 |
| A22 | S. haemolyticus | — | ATCC 29970 |
| A23 | Enterobacter aerogenes | — | ATCC 13048 |
| A24 | Escherichia coli | — | ATCC 4157 |
| A25 | Lactobacillus casei | — | ATCC 393 |
| A26 | Actinomyces pyogenes | — | ATCC 8104 |
| A27 | Erysipelothrix rhusiopathiae | — | ATCC 805 |
| J1 | Citrobacter freundii | — | — |

Preparation of Bacterial Heat Extracts

Tubes of 10 mls of TSB +0.6% YE were inoculated from agar slants or stabs and the organisms were allowed to grow for 4 days at 22° C. The tubes were then centrifuged at 1000 RPM at 25° C. for 10 minutes. The supernatants were aspirated and the pellet resuspended in 1.0 ml of sterile phosphate-buffered saline (PBS). The resuspended pellets were heated in a boiling water bath for 30 minutes and stored at 4° C. until use.

Cultured Cells

P3X63Ag8.653 mouse myeloma cells and L929 mouse fibroblasts (ATCC, Rockville, MD) were cultured in Iscove's modified Dulbecco's medium (Iscove's), (Mediatech Inc., Herndon, VA) containing 10% fetal bovine serum (FBS), (HyClone Laboratories, Inc., Logan, UT). Cultures were maintained in 75 $mm^2$ culture flasks (Corning Glassworks, Corning, NY) in a humidified $CO_2$ incubator (Queue Systems, Inc., Parkersburg, WV) at 37° C. in an atmosphere of 93% air/7% $CO_2$. For fusions, myeloma cells were used in the log phase of growth ($<5 \times 10^5$ cells/ml). For preparation of conditioned medium, L929 cells were cultured as a monolayer for 3 to 4 days. The medium was then harvested, sterile filtered (0.22μ), and stored frozen (−20° C.).

Animals

Female BALB/c (Charles River, Cambridge, Mass.) or CD2F1 (CBA×BALB/c) mice were used at 8 to 12 weeks of age. For ascites production, CD2F1 mice were primed with 2,6,10,14 tetramethyl pentadecane (Pristane), (Aldrich Chemical Co., Milwaukee, WI) 10 to 14 days prior to injection of cells.

Immunizations

BALB/c mice were administered 100 μl of a heat extract from *Listeria monocytogenes* (L1, Dr. R. Flowers, Silliker Lab., Chicago Heights, IL) by subcutaneous injection, then boosted by intraperitoneal injection with the same antigen at weeks 4, 10, and 15. The spleen from the best immune responder as determined by ELISA reactivity was removed 3 days after the final boost and used for a hybridoma fusion.

Cell Fusion

Mouse myeloma cells and immune splenocytes were fused in 50% polyethylene glycol (PEG 1000) (Kodak) at a ratio of 1:5 using a modification of the technique described by Kohler and Milstein (1975). Fused cells were resuspended in 100 ml Iscoves+20% FBS and distributed into ten 96-well microtitration culture plates (Corning) at a density of $2.2 \times 10^5$ cells/well. After 24 hours, HAT selective medium was added [Iscove's+20% FBS containing hypoxanthine (H), aminopterin (A), and thymidine (T)] and the medium changed every 3 to 4 days until macroscopic growth was visible. Cultures showing positive growth in HAT were screened for anti-Listeria monoclonal antibodies as described below. Positive cultures were expanded to 24-well culture plates (Corning) then cloned twice by limiting dilution in Iscove's containing 50% L929-conditioned medium, 20% FBS, and HT, weaning the cells of aminopterin.

ELISA Screening of Hybridomas

Primary Screen

Hybridoma cultures showing macroscopic growth were screened for reactive monoclonal antibodies by ELISA using heat extracted Listeria antigens bound to microtiter plates. For this purpose, Immulon 2 polystyrene plates (flat bottom), (Dynatech Laboratories, Inc. Alexandria, VA) were coated overnight (4° C.) with a heat extract of L1 diluted 1:100 in PBS (100 μ/well). Plates were blocked with PBS containing 3% fish gelatin for 60 minutes (22° C.), then incubated with hybridoma supernatants (100 μ/well) for 60 minutes (37° C.). After 3 washes the plates were incubated for 60 minutes (37° C.) with 0.1 μg/ml horseradish peroxidase-conjugated polyclonal goat antibodies to mouse IgG+IgM+IgA (HyClone Laboratories, Inc., Logan, UT). Following five washes, the plates were developed for 30 minutes (22° C.) with tetramethyl benzidine substrate solution (100 μl/well), (Organon Teknika Corp., Durham, NC) and the chromogenic reaction terminated with 4N $H_2SO_4$ (100 μ/well). Optical density (O.D.) values were determined at 450 nm using an automated plate reader (Model EL309, Bio-Tek Instruments, Inc., Burlington, VT) blanked on air. A positive was interpreted to be an O.D. reading of greater than 0.2.

220 Screening of Hybridomas

Cultures that showed positive reactivity in the primary screen were retested against a panel of Listeria and non-Listeria heat extracts as described above. The panel consisted of *L. monocytogenes, L. innocua*, Streptococcus species, Pseudomonas species, *Salmonella typhi*, and *Escherichia coli*.

Specificity Testing of Anti-Listeria Monoclonal Antibodies

Positive monoclonal antibodies from the secondary screen were tested against a comprehensive panel of Listeria heat extracts using the same ELISA format. Organisms tested included 26 different preparations of *L. monocytogenes*, 2 of *L. ivanovii*, and 1 each of *L. innocua, L. grayi, L. denitrificans, L. murrayi*, and *L. seeligeri*.

A comprehensive panel of gram positive organisms that may grow in the same broth and cause concern for cross-reactivity was tested by ELISA using hybridoma supernatants following the procedure described above. This panel consisted of *Micrococcus varians, Streptococcus cremoris, S. pyogenes, S. bovis, S. thermophilus, S. fecalis, Staphylococcus epidermidis, S. haemolyticus, S. aureus, Actinomyces pyogenes, Bacillus cereus, Lactobacillus casei*, and *Erysipelothrix rhusiopathiae*.

In some instances *S. aureus* and *L. monocytogenes* heat extracts were first centrifuged at 12,000 xg for 5 minutes at 22° C. (Microfuge, Beckman Instruments) to remove bacterial cellular debris. The supernatant was then used for plate coating (1:100) and incubation with hybridoma supernatants as described above.

A panel of heat extracts from gram negative organisms was tested using the same ELISA format, which included *Pseudomonas fluorescens, Citrobacter freundii, Enterobacter aerogenes, Escherichia coli*, and *Salmonella typhi*.

Production and Purification of Monoclonal Antibodies

Ascites growth of hybridoma clones for production of milligram quantities of monoclonal antibodies was achieved by injecting $3.0 \times 10^6$ cells into pristane-primed CD2F1 mice and harvesting fluids 10 to 14 days later. Monoclonal antibody titers were determined by ELISA using *L. monocytogenes* heat extract (L1) bound to microtitration plates as described above. Monoclonal antibodies were affinity-purified by Protein-A sepharose chromatography (Pharmacia, Inc., Piscataway, NJ) and stored at −70° C. until use.

Immunochemical Characterization of Monoclonal Antibodies

Monoclonal antibody subisotype analysis was conducted using a commercial double immunodiffusion kit (ICN Immunobiologicals, Lisle, IL). Identification of target antigens was obtained by Western blot analysis of *L. monocytogenes* heat extract (L1) from SDS-PAGE gels. Proteins were electrophoresed on a discontinuous SDS gradient polyacrylamide gel (5 to 15%) (Laemmli, 1970) and then transferred to nitrocellulose by electroblotting (Towbin, et. al., 1979). The blots were blocked for 2 hours (37° C.) in PBS containing 5% non-fat dry milk, rinsed twice in PBS+0.05% Tween ®20, then labeled as follows: 1 cm strips of the preparative bolt were incubated with individual hybridoma clone supernatants for 2 hours (37° C.) with agitation, then rinsed twice as above and further incubated for 60 minutes, 37° C. with 0.25 μg/ml HRP-conjugated goat antibodies to mouse IgG+IgM (H+L) (Kirkegaard and Perry Laboratories, Gaithersburg, MD). Following two washes, bolts were stained (22° C.) with PBS containing 0.06% diaminobenzidine (Sigma)+0.03% $H_2O_2$.

Several panels of heat extracts from several Listeria and non-Listeria organisms were subjected to analytical SDS-gradient PAGE and Western bolt analysis as described above. The panels consisted of *L. monocytogenes*

(Serotypes 1-4), *L. grayi, L, ivanovii, Linnocua, L. dentrificans, L. seeligeri, L. murrayi, Streptococcus pyogenes, Staphylococcus aureus, Lactobacillus casei, Erysipelothrix rhusiopathiae, Pseudomonas fluorescens, Salmonella typhi* and *Citrobacter freundii*. Select purified monoclonal antibodies (5 μg/ml) were then used to immunostain this antigen panel as described above.

Purification and Conjugation of Antibodies 10-15 ml of ascites was mixed 1:2 with binding buffer pH 9.0, (Affi-Gel Protein A MAPS II BUffers, Bio-Rad Laboratories, Richmond, CA) and loaded onto a 30 ml Protein A column (Sepharose 4B-CL-Protein A, Pharmacia Fine Chemicals, Piscataway, NJ). Antibody was eluted using the elution buffer, pH 3.0 (Bio-Rad). Protein was monitored at 280 nm and fractions collected.

In some cases, these antibodies were further conjugated to horseradish perosidase (Sigma Type VI, St. Louis, MO) using the method of Nakane and Kawaoi (1974).

One Step Capture ELISA Procedure

Immulon Microtiter® plates (Dynatech) were coated overnight (4° C.) with Protein A purified 10-12C (Group II) (100 μl/well) diluted to 10 μg/ml in 0.05 M sodium carbonate/bicarbonate buffer (pH 9.6). The plates were blocked with a protein buffer for 30 min at room temperature. After aspirating the blocking solution, 100 μl of the heat extract and 100 μl of the HRP conjugate 10-2A (Group III) (0.25 μg/ml) were added at the same time (One Step ELISA) and incubated 60 min. at 37° C. After the incubation, plates were washed 6 times and 100 μ/well of tetramethyl-benzidine (KPL) substrate was added. The plate was incubated at room temperature for 30 min then 100 μl/well of 2N H$_2$SO$_4$ was added. The optical density was measured at 450 nm in an automated plate reader (Bio-Tek) blanked on air. 100μl of PBS was used as a negative control.

Modifications of this procedure were performed in some cases by using a different monoclonal on the plates to capture the antigen or using a combination of monoclonals from two or three different Groups. Similar modifications were often performed using other HRP conjugated monoclonals either individually or in combination.

Results

Screening of Hybridoma Cultures

Of 511 hybridomas tested, 37 showed positive ELISA reactivity with the *L. monocytogenes* (L1) heat extract. Positives were then expanded and were retested against a small panel of Listeria and non-Listeria heat extracts to determine their specificity. Fifteen of the 37 hybridoma monoclonal antibodies showed specificity for Listeria. All 15 reacted with both *L. monocytogenes* and *L. innocua*. The remaining 22 monoclonal antibodies showed various reactivity profiles with non-Listeria heat extracts (Streptococcus, Pseudomonas, Salmonella, Escherichia). One of these (10-7C), which reacted with both Listeria and Streptococcus was retained for further study.

A comprehensive panel of Listeria heat extracts was used to ELISA test the 15 anti-Listeria monoclonal antibodies for broad range reactivity. All serotypes of *L. monocytogenes* (1-4) and all other species of Listeria except *L. denitrificans* were detected by the 15 monoclonal antibodies (Table 2).

TABLE 2

| Hybridoma Designation | Screening ELISA Reactivity of MoAbs | | | | | MoAb Isotype |
|---|---|---|---|---|---|---|
| | *L. monocytogenes*[a] | *L. denitrificans*[b] | Other Listeria Species[c] | Non-Listeria Gram(+)[d] | Non-Listeria Gram(−)[e] | |
| 2-1C | + | − | + | − | − | IgG$_1$ |
| 2-3H | + | − | + | − | − | IgG$_1$ |
| 3-1D | + | − | + | − | − | IgG$_1$ |
| 7-5H | + | − | + | − | − | IgG$_1$ |
| 7-6H | + | − | + | − | − | IgG$_1$ |
| 7-8H | + | − | + | − | − | IgG$_{2a}$ |
| 8-7A | + | − | + | − | − | IgG$_{2a}$ |
| 8-8A | + | − | + | − | − | IgG$_1$ |
| 8-6D | + | − | + | − | − | IgG$_{2a}$ |
| 8-9D | + | − | + | − | − | IgG$_1$ |
| 8-4H | + | − | + | − | − | IgG$_1$ |
| 9-5E | + | − | + | − | − | IgG$_1$ |
| 10-2A | + | − | + | − | − | IgG$_{2a}$ |
| 10-11A | + | − | + | − | − | IgG$_1$ |
| 10-7C | + | − | + | − | − | IgG$_1$ |
| 10-12C | + | − | + | − | − | IgG$_1$ |

[a]Serotypes 1a, 1b, ½a, ½b, 3a, 3b, 4b
[b]ATCC manual 1985 reports "Inconsistent with the description of the genus Listeria."
[c]*L. ivanovii* (serotype 5), *L. innocua, L. grayi, L. seeligeri, L. murrayi.*
[d]*Micrococcus varians, Staphylococcus aureus\*, S. epidermidis, S. haemolytocus, Streptococcus cremoris, S. bovis, S. pyogenes, S. thermophilus, S. fecalis, Lactobacillus casei, Actinomyces pyogenes, Bacillus cereus, Erysipelothrix rhusiopathiae.*
\*Centrifugation of heat extract required to remove cell wall material.
[e]*Pseudomonas fluorescens, Citrobacter freundii, Enterobacter aerogenes, Escherichia coli* and *Salmonella typhi.*

A panel of heat extracts from gram positive organisms commonly present in pre-enrichment broths from food samples was tested for ELISA cross-reactivity with the 15 anti-Listeria monoclonal antibodies. All 15 failed to react specifically with these heat extracts (see Table 2). However, the IgG$_{2a}$ monoclonals, including an irrelevant IgG$_{2a}$ control, did show a positive reaction with the *S. aureus* heat extract. This reaction was eliminated by centrifugation of the heat extract to remove cell wall material prior to use for ELISA plate coating. Centrifugation of the Listeria heat extract, however, did not affect monoclonal antibody binding (Table 3). It is also interesting to note that 10-7C (IgG$_1$) bound to all gram positive organisms tested, including *S. aureus* (Table 2). The reactivity of 10-7C with *S. aureus* was not abolished by pre-centrifugation of the heat extract.

TABLE 3

| Hybridoma | Protein A Non-Specific Binding | | | |
|---|---|---|---|---|
| | Listeria monocytogenes Suspended | Listeria monocytogenes Centrifuged | Staphylococcus aureus Suspended | Staphylococcus aureus Centrifuged |
| 2-1C | +2 | +2 | — | — |
| 2-3H | +3 | +3 | — | — |
| 3-1D | +3 | +2 | — | — |
| 7-5H | +2 | +2 | — | — |
| 7-6H | +2 | +2 | — | — |
| 7-8H | +4 | +4 | +2 | — |
| 8-7A | +4 | +4 | +2 | — |
| 8-8A | +2 | +2 | — | — |
| 8-6D | +4 | +4 | +3 | — |
| 8-9D | +3 | +2 | — | — |
| 8-4H | +2 | +2 | — | — |
| 9-5E | +3 | +3 | — | — |
| 10-2A | +3 | +4 | +3 | — |
| 10-11A | +2 | +2 | — | — |
| 10-7C | +2 | +1 | +4 | +3 |
| 10-12C | +3 | +3 | — | — |
| IgG$_1$ control | — | — | — | — |
| IgG$_{2a}$ control | — | — | +2 | — |

Key:
— = <0.2
+1 = 0.2 to 0.5
+2 = 0.5 to 1.0
+3 = 1.0 to 2.0
+4 = >2.0

A panel of heat extracts from gram negative organisms was also tested for ELISA cross-reactivity using the 15 anti-Listeria monoclonal antibodies. None of the anti-Listeria monoclonals produced a positive reaction with any of these organisms (Table 2).

Isotype and Western Blot Analysis

Figure 1:
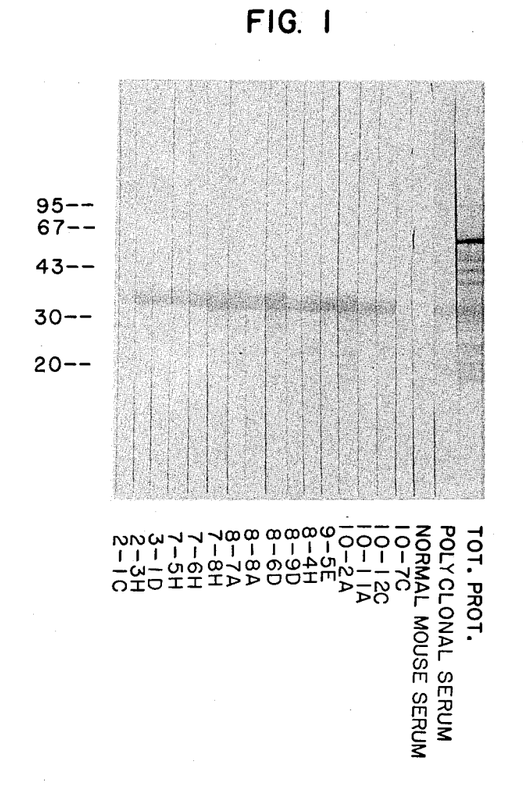
FIG. 1 is a western blot profile of reactivity with heat extract proteins from *Listeria monocytogenes*. The right most column illustrates the profile of the entire heat extract. Columns 1 through 15 illustrate the immunoreactivities of the indicated antibodies with the heat extract.

Isotype analysis of cloned hybridoma supernatants revealed that all 15 produced IgG monoclonals. Eleven were IgG$_1$ and 4 were IgG$_{2a}$. Purified monoclonal antibodies from each of the 15 hybridoma clones were used to probe the *Listeria monocytogenes* (L1) heat extract in Western blots. The 15 Listeria-specific monoclonals recognized a protein antigen with a molecular weight in the range of 30 to 38 KD under both reducing and non-reducing conditions. In addition, the IgG$_{2a}$ (Group III) monoclonals and some of the IgG$_1$ monoclonals (Group II) also recognized lower molecular weight bands (FIG. 1).

Figure 2:
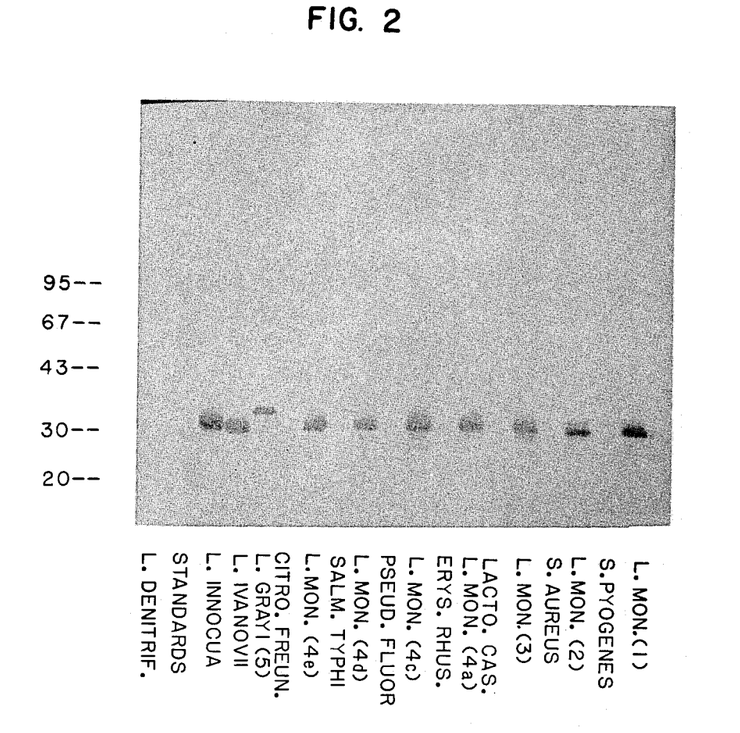
FIG. 2 illustrates the immunoreactivity of monoclonal antibody 10-12C with heat extracts of the indicated species of Listeria and other bacteria.
Figure 3:
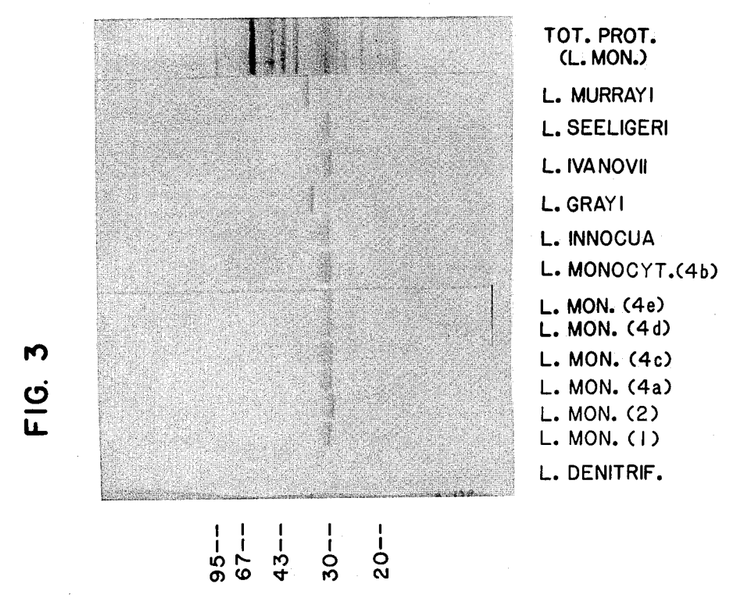
FIG. 3 illustrates the immunoreactivity of the monoclonal antibody 10-12C with the indicated species of Listeria.
Figure 4:
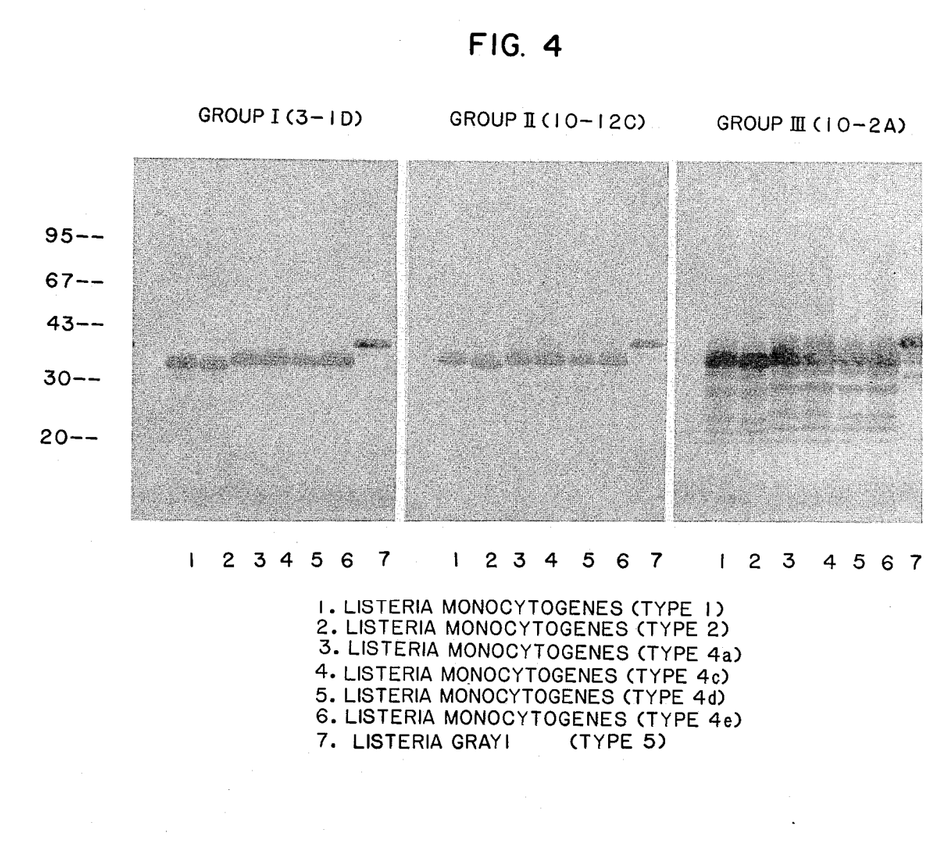
FIG. 4 illustrates the immunoreactivity of 3 of the monoclonals, which recognize distinct epitopes on the major antigen, with the indicated species of Listeria.

To further analyze the antigen distribution and size, heat extracts from both Listeria and non-Listeria were electrophoresed, blotted, and probed with select anti-Listeria monoclonals. Only the Listeria heat extracts were found to contain the antigen recognized by the monoclonals (FIG. 2). Interestingly, a slight variation in molecular weight of the major antigen (30 to 38 KD) was observed between the different serotypes of *L. monocytogenes* (FIG. 3). It is further interesting to note that the *L. grayi* and *L. murrayi* antigens were approximately 5 KD larger than any of the *L. monocytogenes* antigens. In agreement with the ELISA results, *L. denitrificans* did not contain the antigen recognized by the anti-Listeria monoclonals (FIGS. 2 and 3). Furthermore, none of the non-Listeria heat extracts contained this antigen (FIG. 2). These results were consistent regardless of which anti-Listeria monoclonal antibody was tested. 10-7C, however, which has a different ELISA reactivity profile, did not react with any of the Listeria polypeptide antigens in the Western blots (FIG. 1).

The 30 to 34 KD and 34 to 38 KD major antigen, the molecular size varying slightly but reproducably with species, always contains three epitopes. Each monoclonal antibody identified as immunospecific for this antigen reacts with one of these 3 epitopes. Two of these three epitopes so defined also appear in antigens having molecular size ranging between 17 KD and the molecular size of the major antigen.

Typical ELISA results are shown in Table 4. When one antibody of Group II (10-12C) is used on the plate as a capture, and another antibody of Group III (10-2A) is HRP labeled and used as the conjugate, heat extracts of all tested Listeria are easily identified as positive by this assay and heat extracts of all tested non-Listeria are easily identified as negative. In most cases, the Listeria heat extracts could be diluted 2-4 log 10 dilutions and remain positive.

TABLE 4

| Organism | One Step Capture ELISA Results | |
|---|---|---|
| | Dilution | O.D.$_{450}$ |
| Negative Control (PBS) | — | 0.084 |
| *L. monocytogenes* (L1) | 1:100 | >3.0 |
| *L. monocytogenes* (L1) | 1:1000 | 1.245 |
| *L. monocytogenes* (L1) | 1:10,000 | 0.386 |
| *L. grayi* | 1:100 | >3.0 |
| *L. grayi* | 1:1000 | 0.645 |
| *L. ivanovii* | 1:100 | 2.205 |
| *L. ivanovii* | 1:1000 | 0.482 |
| *L. innocua* | 1:100 | >3.0 |
| *L. innocua* | 1:1000 | 1.487 |
| *L. innocua* | 1:10,000 | 0.405 |
| *L. seeligeri* | 1:100 | 1.769 |
| *L. seeligeri* | 1:1000 | 0.496 |
| *L. murrayi* | 1:100 | 1.512 |
| *L. murrayi* | 1:1000 | 0.468 |
| *Staphylococcus aureus* | 1:10 | 0.144 |
| *Staphylococcus faecalis* | 1:10 | 0.138 |
| *Lactobacillus casei* | 1.10 | 0.149 |
| *Actinomyces pyogenes* | 1:10 | 0.131 |
| *Erysipelothrix rhusiopathiae* | 1:10 | 0.091 |

Deposits of F61/9-5E (9-5E), F61/10-12C (10-12C), and F61/10-2A (10-2A) were deposited with the ATCC under Budapest Treaty requirements Aug. 7, 1987.

REFERENCES

ATCC Catalogue of Bacteria, Phages, and rDNA Vectors, 16th edition, 1985, p. 96.

Goding, J., 1978, J. Imm. Meth. 20:241.

Kohler, G. and C. Milstein, 1975, Nature (London) 256:495.

Laemmli, U. K., 1970, Nature 227: 680.

Nakane, P. K. and A. Kawaoi, 1974, J. Histochem. Cytochem 22:1084

Towbin H., T. Staehelin, and J. Gordon, 1979, P.N.A.S. (U.S.A.) 76:4350.

We claim:

1. A Listeria antigen comprising a protein found in Listeria heat extracts, said antigen having a molecular weight of from about 30 to about 38 KD, the antigen comprising three immunogenically different epitopes to which antibodies produced by spleen cells of mice immunized with said Listeria heat extracts are specifically reactive, said antigen being found in heat extracts of all species of Listeria except *L. dentirificans* and not found in *Micrococcus varians, Staphylococcus aureus, S. epidermidis, S. haemolyticus, Streptococcus cremoris, S. bovis, S. pyrogenes, S. thermophilus, S. fecalis, Lactobacillus casei, Actinomyces pyogenes, Bacillus cereus, Erysipelothrix rhusiopathiae, Pseudomonas fluorescens, Citrobacter freundii, Enterobacter aerogenes, Escherichia coli* or *Salmonella typhi*.

2. The Listeria antigen of claim 1, from *L. grayi* or *L. murrayi*, having a molecular weight of about 34 to about 38 KD.

3. The Listeria antigen of claim 1, from *L. monocytogenes*, having a molecular weight of from about 30 to about 34 KD.

4. The Listeria antigen of claim 1, from *L. ivanovii*, having a molecular weight of from about 30 to 34 KD.

5. The Listeria antigen of claim 1, from *L. innocua*, having a molecular weight of from about 30 to about 34 KD.

6. The Listeria antigen of claim 1, from *L. seeligeri*, having a molecular weight of from about 30 to about 34 KD.

7. An immunoassay test kit for detecting the Listeria antigen of claim 1, comprising at least one monoclonal antibody immunoreactive with one of said three immunogenically different epitopes on said antigen.

8. The test kit of claim 7, comprising at least two monoclonal antibodies, at least one which is immunoreactive with one of the three immunogenically different epitopes on said antigen and at least one of which is immunoreactive with one of the other of said epitopes and bound to a detectable label.

9. A monoclonal antibody immunoreactive with the Listeria, antigen of claim 1.

10. The monoclonal antibody of claim 9 selected from the group consisting of an $IgG_1$ antibody and an $IgG_{2a}$, antibody.

11. The monoclonal antibody of claim 9, produced by immunizing an animal with Listeria heat extracts, immortalizing antibody producing cells from said animal, culturing the immortalized cells to produce antibodies, and selecting immortalized cells that produce antibodies immunoreactive with the antigen.

12. The monoclonal antibody of claim 9, which is also immunoreactive with a Listeria antigen comprising a protein found in Listeria heat extracts having a molecular size of less than 30 KD the major antigen but at least 17 KD.

13. The monoclonal antibody of claim 9 having the essential characteristics of the antibody produced by cell line F61/9-5E, ATCC deposit number HB9493.

14. The monoclonal antibody of claim 9 having the essential characteristics of the antibody produced by a cell line F61/10-12C, ATCC deposit number HB9494.

15. The monoclonal antibody of claim 9 having the essential characteristics of the antibody cell line F61/10-2A, ATCC deposit number HB9492.

16. A Listeria antigen comprising a protein found in Listeria heat extracts, said antigen having a molecular weight less than 30 KD but at least 17 KD, and said antigen containing an epitope which is also present on a 30-30 KD protein antigen found in heat extracts of all species of Listeria except *L. denitrificans* and not found in *Micrococcus varians, Staphylococcus aureus, S. epidermidis, S. haemolyticus, Streptococcus cremoris, S. bovis, S. pyrogenes, S. thermophilus, S. fecalis, Lactobacillus casei, Actinomyces pyogenes, Bacillus cereus, Erysipelothrix rhusiopathiae, Pseudomonas fluorescens, Citrobacter freundii, Enterobacter aerogenes, Escherichia coli* or *Salmonella typhi*.

* * * * *

UNITED STATES PATENT AND TRADEMARK OFFICE
CERTIFICATE OF CORRECTION

PATENT NO. : 4,950,589

DATED : August 21, 1990

INVENTOR(S) : Bryan T. Butman and Jerome A. Mattingly

It is certified that error appears in the above-identified patent and that said Letters Patent is hereby corrected as shown below:

Column 12, line 34
    Claim 16, line 5, delete "30-30KD" and substitute -- 30-38KD -- therefor.

Signed and Sealed this

Fourteenth Day of January, 1992

Attest:

HARRY F. MANBECK, JR.

*Attesting Officer*      *Commissioner of Patents and Trademarks*